US00PP18997P3

(12) United States Plant Patent

Goffreda et al.

(10) Patent No.: US PP18,997 P3

(45) Date of Patent: Jul. 1, 2008

(54) PEACH TREE NAMED 'NJF16'

(50) Latin Name: *Prunus persica* L
Varietal Denomination: NJF16

(75) Inventors: Joseph C. Goffreda, Manalapan, NJ (US); Anna M. Voordeckers, East Windsor, NJ (US)

(73) Assignee: Rutgers The State University, New Brunswick, NJ (US)

( * ) Notice: Subject to any disclaimer, the term of this patent is extended or adjusted under 35 U.S.C. 154(b) by 199 days.

(21) Appl. No.: 11/333,521

(22) Filed: Jan. 17, 2006

(65) Prior Publication Data

US 2007/0169237 P1 Jul. 19, 2007

(51) Int. Cl.
*A01H 5/00* (2006.01)

(52) U.S. Cl. ..... Plt./197

(58) Field of Classification Search ..... Plt./197
See application file for complete search history.

*Primary Examiner*—Annette H Para

(74) *Attorney, Agent, or Firm*—James A. Lucas; Driggs, Hogg, Dougherty & Del Zoppo, CO. LPA

(57) ABSTRACT

A new and distinct peach variety of *Prunus persica* named 'NJF16' is provided. This variety is distinguished from other peach varieties by its unique combination of large, showy, light pink flowers, flat fruit that ripen in early midseason, bright golden-yellow fruit that are devoid of over color, clingstone fruit with a juicy, nonmelting texture and sweet, spicy flavor, firm fruit that retain their firmness well and trees with regular, heavy production of fruit.

6 Drawing Sheets

Latin name of genus and species of the plant claimed: *Prunus persica* L.

BACKGROUND OF THE INVENTION

The present invention relates to a new and distinct variety of peach tree named 'NJF16'. Our new tree resulted from crossing 'A43-143-782081' as the seed parent with 'NJF4' peach tree, as the pollen parent. The new variety differs from seed parent 'A43-143-782081' (unpatented) in that the new variety has flat fruit while the parent has round fruit. The new variety differs from pollen parent 'NJF4' (unpatented) in that the new variety has no blush and a golden yellow ground color while the parent has a light blush and a yellow-green ground color. The resulting tree was selected when growing in a cultivated area as the 134$^{th}$ tree in the 91$^{st}$ row of Block D in Cream Ridge, N.J.

BRIEF SUMMARY OF THE INVENTION

The 'NJF16' variety is distinguished from other peach varieties due to the following unique combination of characteristics:

Flat fruit shape.

Fruit devoid of over color.

Fruit with a bright golden-yellow ground color.

Fruit with a sweet, spicy flavor.

Nonmelting flesh texture.

Very firm fruit that retain their firmness well.

Regular and heavy production of fruit.

The variety was asexually reproduced at the Rutgers Fruit Research and Extension Center in Cream Ridge, N.J. Asexual reproduction of this new variety by budding onto 'Lovel' rootstock (unpatented) for several generations shows that the foregoing characteristics are so reproduced.

The following detailed description concerns the original tree, 'NJF16'. The original tree and progeny have been observed growing in a cultivated area in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
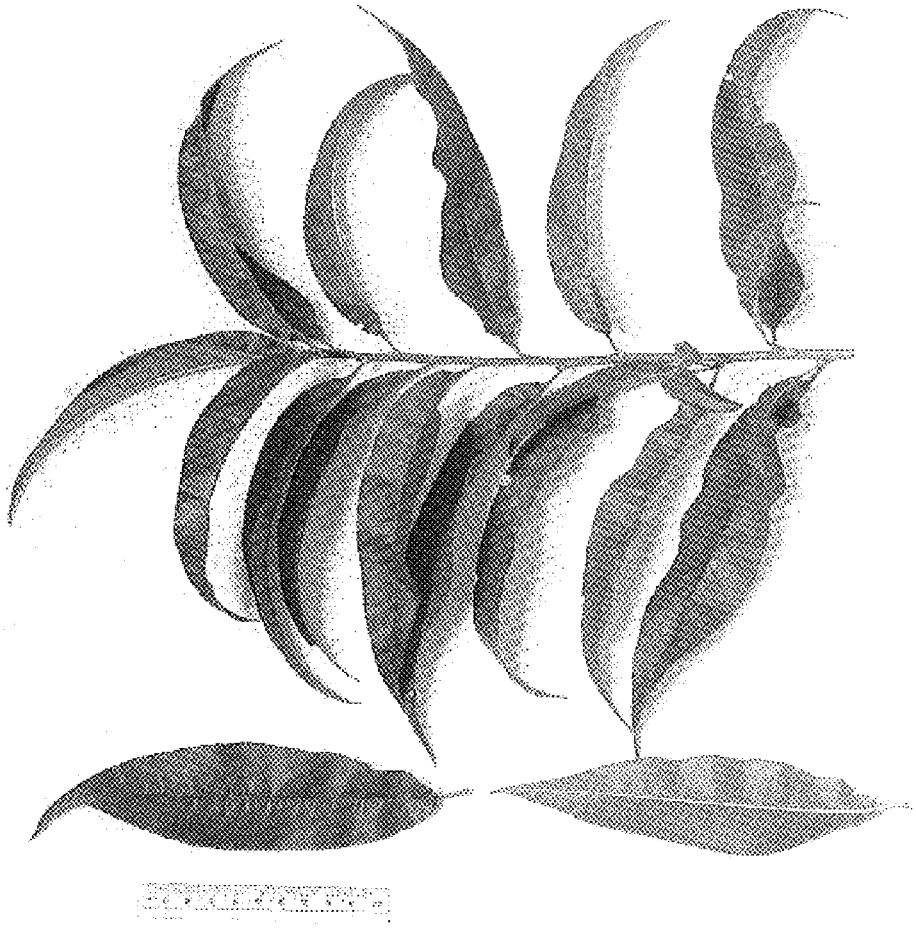
FIG. 1 is a color photograph taken on Aug. 29, 2005 of a characteristic twig of 'NJF16' in late summer bearing typical leaves of the mature foliage.
Figure 2:
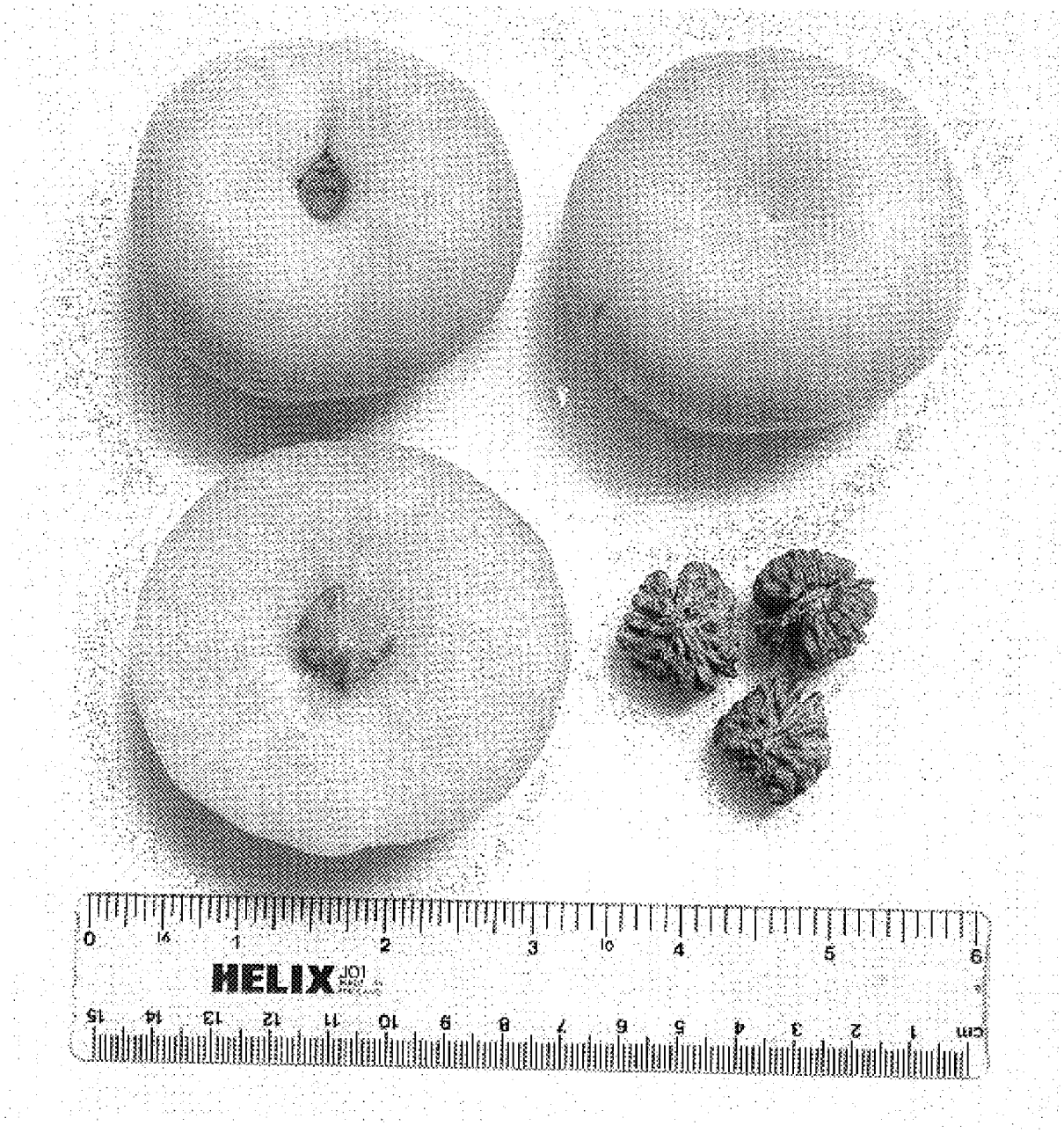
FIG. 2 is a color photograph of mature fruit of 'NJF16' and stones harvested in Cream Ridge, N.J. on Aug. 14, 2003. Whole fruit are presented in two positions and a cross section to show that the pericarp adheres to the pit when the fruit is mature. The stones illustrate the high, narrow, and deep dorsal ridge on the stone and the mixture of pits and chains of pits forming grooves on the surface of the stone.
Figure 3:
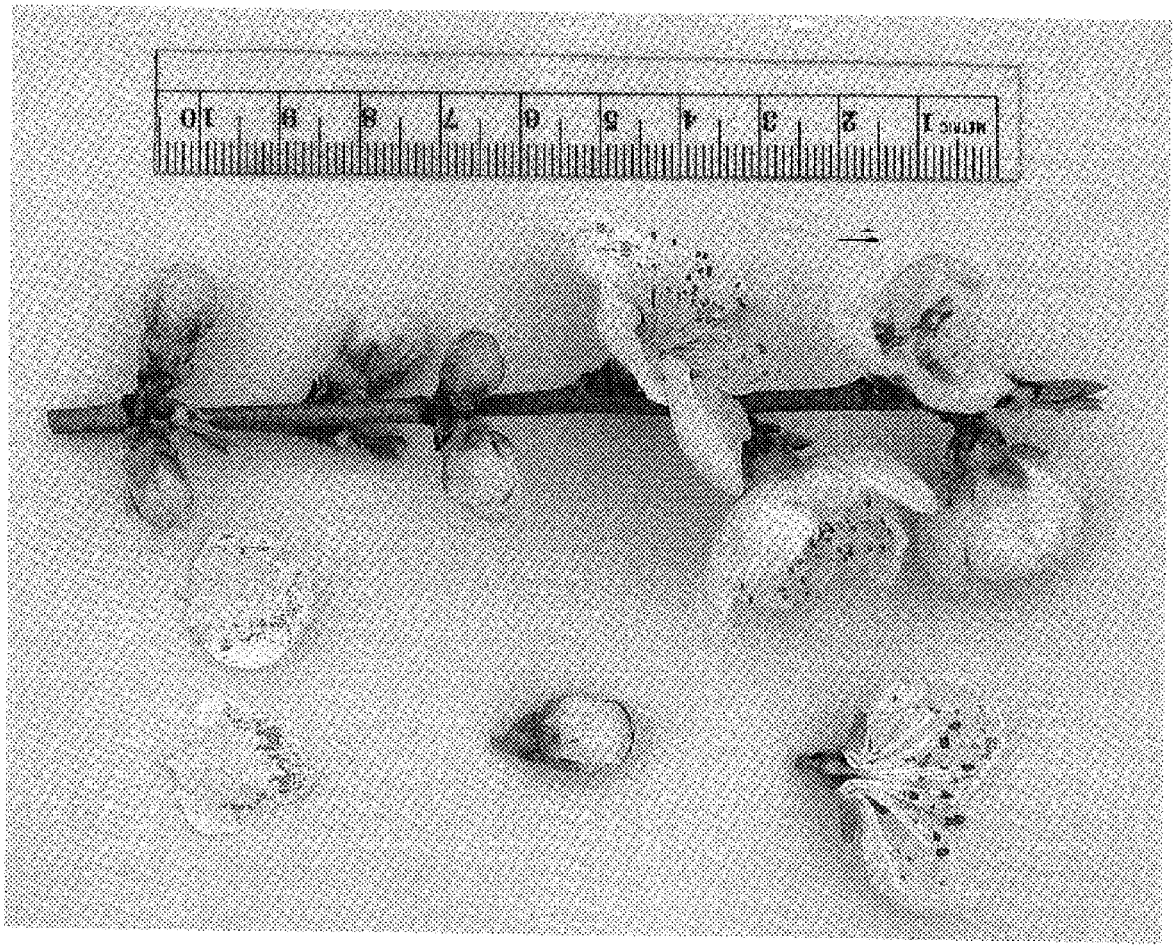
FIG. 3 is a color photograph of a characteristic twig that illustrates the typical flower buds and showy light pink flowers of 'NJF16' observed on a in Cream Ridge, N.J. on Apr. 21, 2004.
Figure 4:
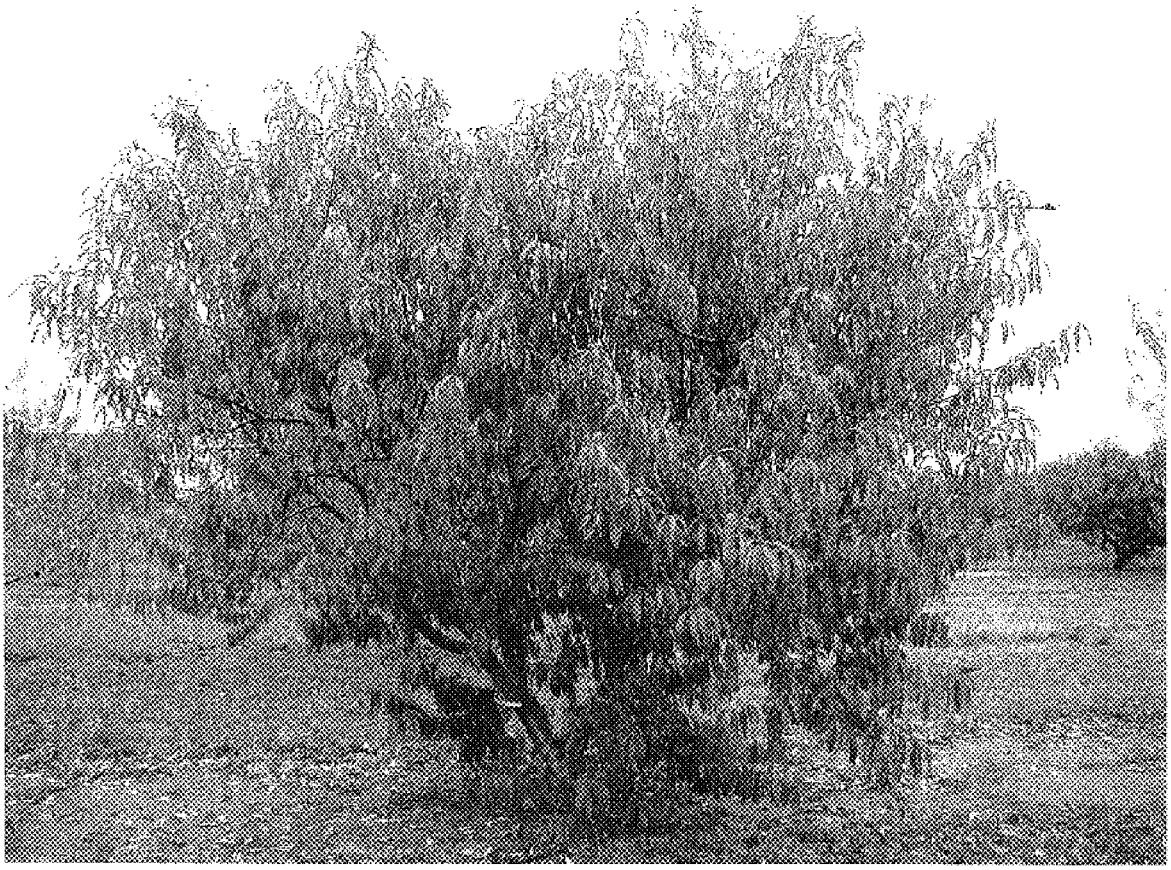
FIG. 4 is a color photograph of a tree of 'NJF16' in early fall that illustrates the moderately spreading growth habit of a tree in Cream Ridge, N.J. on Oct. 27, 2005.
Figure 5:
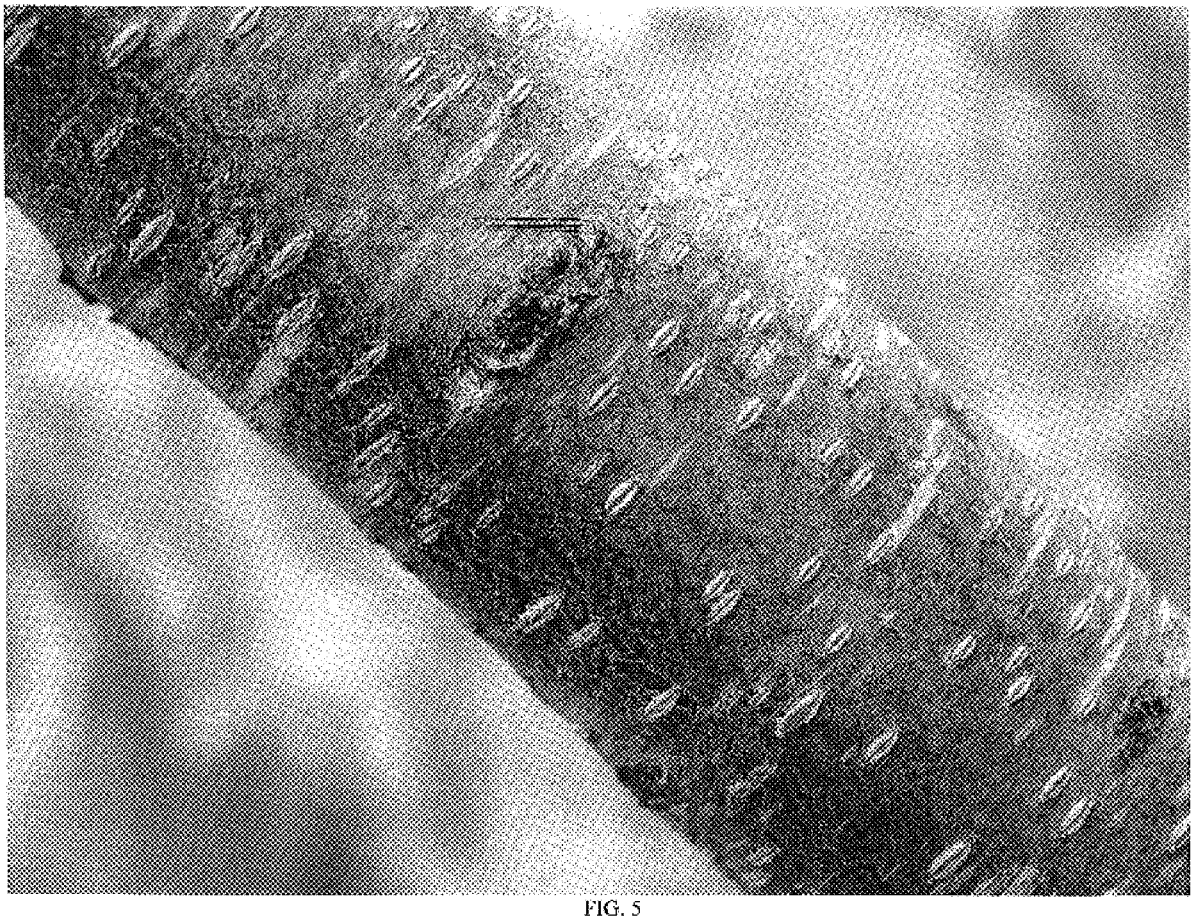
FIG. 5 is a color photograph taken on Oct. 27, 2005 of immature bark of 'NJF16' that illustrates color and the moderate density of long lenticels on the immature bark.
Figure 6:
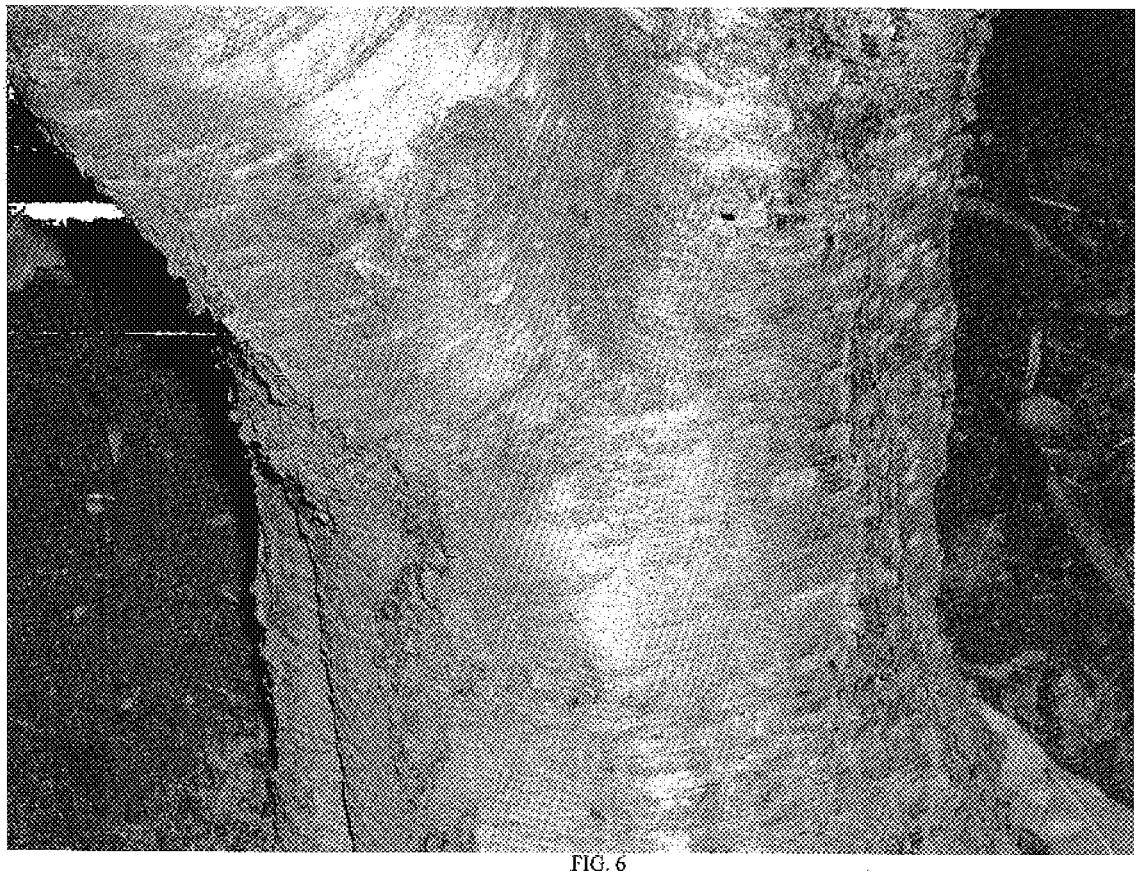
FIG. 6 is a color photograph taken on Oct. 27, 2005 of mature bark of 'NJF16' that illustrates the moderately rough texture of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJF16' variety is based on observations of the original seedling tree. The observed tree was seven years of age and growing on 'Lovell' seedling rootstock (unpatented) in Cream Ridge, N.J.

Latin name of genus and species: *Prunus persica* L.
Parentage:

| | |
|---|---|
| Seed parent: | A43-143-782081 |
| Pollen parent: | NJF4 |

Tree:

| | |
|---|---|
| Vigor: | Vigorous. |
| Plant hardiness zone: | Growth of plants has only been observed in zone 6b. |
| Dormant flower bud cold tolerance: | At least to −16° C. |
| Overall shape: | Moderately spreading with a well rounded canopy. |
| Height: | Above average as compared to other peach cultivars. For example, measurement of a typical grafted tree on 'Lovell' seedling rootstock (unpatented) at seven years after planting shows an average height of four meters when grown in Cream Ridge, New Jersey. |
| Width: | Average as compared to other peach cultivars. For example, measurement of a typical grafted tree on 'Lovell' seedling rootstock (unpatented) at seven years after planting shows an average width of six meters when grown in Cream Ridge, New Jersey. |
| Caliper: | Seven year old tree is 60 cm in circumference measured at 20 cm from the ground |

Trunk:

| | |
|---|---|
| Trunk bark texture: | Slightly rough. |
| Trunk bark color: | Under color is RHS 156A overlaid by RHS 200C. |
| Primate branches: | Branches are RHS 178A in color, overlaid with RHS 196D; a tree that is pruned using the standard open center system will annually produce numerous upright shoots consisting entirely of one year wood, a typical example of which averages 1.7 m in length and 2.3 cm in diameter at the base, with lateral branches borne at crotch angles of 50 degrees. |
| Lenticels: | Moderate density, approximately two per square cm; typical examples of which measured 6 mm in length; RHS 177C in color, bordered with RHS 198D. |
| Branch pubescence: | None. |
| New growth bark: | Color RHS 178B in sun; between RHS 152B to RHS 152C in shade. |
| Internodes: | Length 10 mm to 25 mm, averaging 23 mm on a one-year shoot. |

Leaves:

| | |
|---|---|
| Texture: | Glabrous. |
| Sheen: | Young leaves semi-glossy with a flat finish on the underside. |
| Length: | About 142 mm to 185 mm, averaging about 160 mm including the petiole. |
| Width: | About 35 mm to 47 mm, averaging about 40 mm. |
| Petiole: | About 12.5 mm long and about 1.5 mm in diameter. |
| Margin: | Sinuate and finely serrate. |
| Margin undulation: | Medium. |
| Form: | Lanceolate. |
| Apex: | Sharply acute, curved downward. |
| Base: | Broadly acute. |
| Venation: | Pinnate. |
| Glands: | |
| Number: | About 3 to 5, averaging about 3.6. |
| Position: | Located on petiole and leaf margin. |
| Size | Length averaging 1.0 mm and width averaging 0.9 mm. |
| Form: | Reniform. |
| Stipules: | None observed on mature leaves. |
| Leaf Color: | |
| Upper leaf surface: | RHS 147A. |
| Lower leaf surface: | RHS 147B. |
| Vein | RHS 160B to RHS 160C. |
| Pubescence | None. |

The length, width, thickness, and other measurements were obtained from observations of twenty typical leaves 2004.
Flowers:

| | |
|---|---|
| Size: | Large size, typical flower measuring about 39.5 mm across. |
| Color: | |
| Dormant bud: | Between RHS 201B and RHS 197C. |
| Pink stage bud: | Between RHS 56A and RHS 56B. |
| Open flower: | Young open flowers RHS 56C, and remaining RHS 62D at petal fall. |
| Petals: | Typically five petals per flower; nearly round shape; about 19.5 mm long and 18 mm wide. RHS 62D in color. |
| Petal apex: | Obtuse. |
| Petal base: | Acute. |
| Stamens: | |
| Number: | Variable, between 39 to 43, averaging about 41. |
| Length. | Variable, between 9.8 mm to 13.7 mm, averaging 12.1 mm. |
| Filament color: | RHS 157B. |
| Anther color: | RHS 42B. |
| Pistil: | |
| Number: | One. |
| Size: | Length between 12.9 and 14.7 mm, averaging about 14 mm. |
| Pistil color: | RHS 144C. |
| Ovary: | Moderately pubescent, and oblate in shape. |
| Sepals: | |
| Number: | Five. |
| Color: | Between RHS 147A and RHS 199B in color, with light pubescence. |
| Shape: | Triangular, with a rounded apex. |
| Size: | Length averaging 4.8 mm, width averaging 3.8 mm. |
| Nectar cup color: | RHS 167C. |
| Pollen: | Abundant; RHS 20A in color. |
| Fragrance: | Very slight. |
| Bloom season: | Onset of bloom on April 18; full bloom on April 20; petal fall on April 23. |

Fruit: (Observations from a limited number of typical fruit grown in Cream Ridge, N.J.).

| | |
|---|---|
| Size | Large for a flat peach, about 3.9 cm long, 6.5 cm wide parallel to the suture, and 7.0 cm wide perpendicular to the suture. |
| Typical weight: | 106.9 g |
| Form: | |
| Longitudinal section | Oblate. |
| Traverse section: | Nearly round. |
| Suture: | Very shallow. |
| Ventral surface: | Rounded. |
| Base: | Truncated and indented. |
| Apex: | Depressed; between nearly 0 to about 5 mm in diameter, with an average of 3.6 mm. |
| Stem: | Average length of 8.8 mm and an average diameter of 9.8 mm. |
| Skin: | |
| Thickness: | Average. |
| Surface: | Regular with short pubescence. |
| Tenacity: | Above average. |
| Astringency: | None. |
| Tendency to crack: | Low. |
| Color: | Over color none; under color RHS 16B. |
| Fruit Properties: | |
| Flesh color | Between RHS 15B. |
| Flesh adhesion: | Clingstone. |
| Juice: | Moderate. |
| Texture: | Fine, nonmelting. |
| Fibers: | Not noticeable. |
| Ripens: | Between July 23 and August 5 at Cream Ridge, New Jersey. |
| Flavor: | Spicy. |
| Soluble solids: | 10.9%. |
| Aroma: | Strong. |
| Eating quality: | Excellent. |
| Keeping quality: | Good. Has held its flavor and firmness for at least 21 days in cold storage at 1° C. to 4° C. |
| Shipping quality: | Fair. Although no bruising or scaring disorders have been observed, lack of red over color makes blemishes more visible. |

-continued

| | |
|---|---|
| Usage | Desert. |
| Market: | Local and long distance. |
| Productivity: | Excellent for a flat peach. Tree has produced a crop in eight out of eight years, and a full crop in six out of eight years at Cream Ridge, New Jersey. |

Stone:

| | |
|---|---|
| Type: | Clingstone. |
| Form: | Oblate. |
| Base: | Very broad. |
| Apex: | Very broad. |
| Surface: | Mixture of pits and chains of pits forming grooves. |
| Dorsal ridge: | High, narrow, and deep lines. |
| External Color: | Between RHS 165B and RHS 165D. |
| Internal color when cracked: | Between RHS 165C and RHS 165D. |
| Cavity surface color: | RHS 165C. |
| Average stone weight: | Dry weight 5.7 g. |
| Average stone wall thickness: | 4.3 mm. |
| Size: | Averages about 15.0 mm long 22.2 mm wide parallel to the dorsal ridge, and 20.9 mm wide perpendicular to the dorsal ridge |
| Tendency to split: | None. |
| Kernel: | |
| Form: | Irregular. |
| Skin color: | RHS 163A. |
| Vein color: | RHS 167D. |
| Viable: | No. |
| Size: | Highly variable; forms only rudimentary seed. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *